(12) United States Patent
Dansereau et al.

(10) Patent No.: US 6,569,460 B1
(45) Date of Patent: May 27, 2003

(54) FILM-COATED TABLET FOR IMPROVED UPPER GASTROINTESTINAL TRACT SAFETY

(75) Inventors: Richard John Dansereau, Mason, OH (US); Petrus Jakobus Bekker, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/694,799

(22) Filed: Oct. 23, 2000

Related U.S. Application Data

(63) Continuation of application No. 09/095,322, filed on Jun. 10, 1998, now Pat. No. 6,165,513.
(60) Provisional application No. 60/049,306, filed on Jun. 11, 1997.

(51) Int. Cl.$^7$ .......................... A61K 31/135; A61K 9/20
(52) U.S. Cl. ....................... 424/490; 424/463; 424/464; 424/482; 424/486; 424/489; 514/652; 514/821; 514/960; 514/961; 514/962
(58) Field of Search ................ 424/463, 464, 424/482, 489, 490, 484; 514/821, 652, 960–962

(56) References Cited

U.S. PATENT DOCUMENTS

| | | | | |
|---|---|---|---|---|
| 4,161,530 A | * | 7/1979 | Koella | 424/274 |
| 5,146,730 A | * | 9/1992 | Sadek et al. | 53/454 |
| 5,658,589 A | * | 8/1997 | Parekh et al. | 424/463 |
| 5,667,804 A | * | 9/1997 | Wong et al. | 424/472 |

* cited by examiner

*Primary Examiner*—Bennett Celsa
(74) *Attorney, Agent, or Firm*—Mary Pat McMahon

(57) ABSTRACT

A novel oral dosage to be delivered to the stomach comprising a safe and effective amount of an active ingredient selected from the group consisting of emepronium bromidebromide, doxycycline, and other tetracyclines/antibiotics, iron preparations, quinidine, nonsteroidal anti-inflammatory drugs, alprenolol, ascorbic acid, captopril, theophylline, zidovoudine (AZT), bisphosphonates and mixtures thereof and pharmaceutically-acceptable excipients, wherein said oral dosage form is a generally oval form and film coated to facilitate rapid esophageal transit and avoid irritation in the mouth, buccal cavity, pharynx, and esophagus.

7 Claims, 1 Drawing Sheet

FILM-COATED TABLET FOR IMPROVED UPPER GASTROINTESTINAL TRACT SAFETY

CROSS REFERENCE

This application is a continuation of Ser. No. 09/095,322 (Jun. 10, 1998) U.S. Pat. No. 6,165,513 which claims priority under Title 35, United States code 119(e) from Provisional Application Ser. No. 60/049,306 filed Jun. 11, 1997.

TECHNICAL FIELD

The present invention relates to novel oral dosage forms that protect the epithelial and mucosal tissues of the mouth and the buccal cavity, the pharynx, the larynx, and the esophagus from erosion, ulceration, or other like irritation suffered by direct contact of these tissues with the active ingredient. The tablet is a modified oval shape and is film coated. This invention further relates to a method of treating or preventing diseases characterized by abnormal calcium and phosphate metabolism using the novel film coated dosage forms described herein.

BACKGROUND OF THE INVENTION

The oral administration of certain active ingredients sometimes results in patient complaints shortly after dosing; said complaints are usually characterized by the patients as heartburn, esophageal burning, pain and/or difficulty upon swallowing, and/or pain existing behind and/or mid-sternum. It is believed that these complaints originate from esophagitis or esophageal irritation caused by the erosion, ulceration, or other like irritation of the epithelial and mucosal tissues of the upper gastrointestinal tract, generally the mouth through the stomach, most generally the esophagus. It is hypothesized that said irritation results from the active ingredient coming in direct contact with those epithelial and mucosal tissues, resulting in the topical irritation thereof. If the dosage form adheres in the esophagus, the active ingredient slowly dissolves and creates a high drug concentration on the mucosal surface of the esophagus.

Particularly problematic drugs are those which when dissolved have a pH below 2–3, drugs with cytotoxic activity (caustic) and/or the local development of a hyperosmolar solution which causes mucosal desiccation. These actives include but are not limited to emperonium bormide, doxycycline, and other tetracyclines/antibiotics, iron preparations, quinidine, nonsteroidal anti-inflammatory drugs, alprenolol, ascorbic acid, captopril, theophylline, zidovoudine (AZT) and bisphosphonates.

Dosage forms have been developed to delay the release of the active ingredients after passage through the upper gastrointestinal tract and in some cases through the stomach, i.e., enteric coated tablets. But, in certain instances its is undesirable or unnecessary for a medicant to be in a delayed release dosage form. Accordingly, it became desirable to develop novel oral dosage forms which would facilitate rapid esophageal transit, minimize or avoid the release of an active compound in the upper gastrointestinal tract and deliver the active ingredient to the stomach. Said novel oral dosage forms are generally oval shaped tablets, including but are not limited to oval, modified oval and caplet shaped tablets and are film coated to facilitate rapid esophageal transit and release the active in the stomach thereby, providing protection to the tissues of the mouth, pharynx, and esophagus. Most preferred are novel modified oval shape, film coated oral dosage forms that contain a bisphonates such as risedronate or alendronate.

SUMMARY OF THE INVENTION

The present invention is directed to a pharmaceutical formulation in an oral generally oval shaped, including but not limited to oval, modified oval and caplet shaped form. The dosage form is film coated and comprised of a safe and effective amount of an active ingredient and pharmaceutically-acceptable excipients. Said dosage forms facilitate rapid esophageal transit time thereby avoiding the release of active ingredient in the buccal cavity, pharynx, and esophagus and protecting the epithelial and mucosal tissues thereof from erosion, ulceration or other like irritation.

Accordingly, the novel dosage forms described herein effect the delivery to the stomach of said human or other mammal of a safe and effective amount of active ingredient, and substantially alleviates esophagitis or esophageal irritation which sometimes accompanies the oral administration of certain active ingredients.

The invention further comprises a method of treating diseases characterized by abnormal calcium and phosphate metabolism comprising administering to a human or other mammal afflicted with such a disease a novel oral dosage form containing a bisphosphonate as described herein.

DETAILED DESCRIPTION OF THE PRESENT INVENTION

Figure 1:
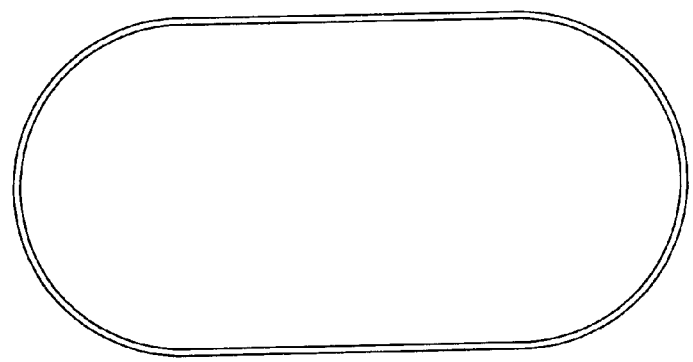
FIG. 1 shows a top plan view of a modified oval tablet.

The present invention is directed to a novel generally oval shaped, film coated oral dosage form comprising a safe and effective amount of an active ingredient and pharmaceutically-acceptable excipients. Said dosage forms facilitates rapid esophageal transit thereby avoiding or minimizing the release of the active ingredient in the mouth, pharynx, and esophagus and protecting the epithelial and mucosal tissues thereof from erosion, ulceration or other like irritation. Particularly preferred are modified oval shaped, film coated oral dosage forms.

Accordingly, the said dosage forms effect the delivery to the stomach of said human or other mammal of a safe and effective amount of the active ingredient, and substantially alleviate esophagitis or esophageal irritation which occasionally accompanies the oral administration of active ingredients.

The invention further comprises a method of treating diseases characterized by abnormal calcium and phosphate metabolism comprising administering to a human or other mammal afflicted with such a disease a novel oral form as described herein.

A. The Active Ingredient

The active ingredient herein may be any ingredient that yields a therapeutic benefit and is required to be delivered to the stomach of said human or other mammal. The benefits of the present invention are particularly realized when the active ingredient if released prior to entering the stomach may cause patient complaints such as heartburn, esophageal burning, pain and/or difficulty upon swallowing, and/or pain existing behind and/or mid-sternum. Such active ingredients are those which when dissolved have a pH below 2–3, drugs with cytotoxic activity (caustic) and/or the local development of a hyperosmolar solution which causes mucosal desiccation. Preferred actives are selected from the group consisting of emperonium bormide, doxycycline, and other tetracyclines/antibiotics, iron preparations, potassium chloride, quinidine, nonsteroidal anti-inflammatory drugs, alprenolol, ascorbic acid, captopril, theophylline, zidovoudine (AZT) and bisphosphonates. More preferred actives are risedronate, alendronate and pamidronate, most preferred is risedronate.

The disphosphonates of the present invention are structural variations of the geminal grouping:

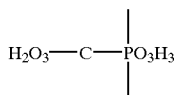

The term "risedronate", as used herein, denotes the disphosphonate compound 3-pyridyl-1-hydroxyethylidene-1,1-bisphosphonic acid and has the following structure:

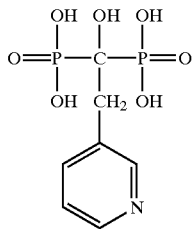

The compound risedronate is further described in U.S. Pat. No. 5,583,122, Benedict et al., assigned to the Procter & Gamble Co., issued Dec. 10, 1996, and "An American Conference, Bisphosphonates: Current Status and future Prospects, The Royal College of Physicians, London, England, May 21–22, 1990, organized by IBC Technical Services, both references hereby are incorporated by reference.

The term "risedronate active ingredient" includes risedronate, risedronate salts, and risedronate esters, or any mixture thereof. Any pharmaceutically-acceptable, non-toxic salt or ester of risedronate may be used as the risedronate active ingredient in the novel oral dosage forms of the present invention. The salts of risedronate may be acid addition salts, in particular the hydrochloride, but any pharmaceutically-acceptable, non-toxic organic or inorganic acid salt may be used. In addition, salts formed with the phosphonic acid group may be used, including, but not limited to alkali metal salts (K, Na) and alkaline earth metal salts (Ca, Mg) the Ca and Na salts being preferred.

Particularly, other esters of risedronate which are suitable for use as the active ingredient herein are straight chain or branched $C_1$–$C_{18}$ alkyl esters, including, but not limited to, methyl, ethyl, propyl, isopropyl, butyl, isobutyl, amyl, hexyl, heptyl, octyl, nonyl, decyl, lauryl, myristyl, cetyl, and stearyl; straight chain or branched $C_2$–$C_{18}$ alkenyl, esters, including but not limited to vinyl, alkyl, undecenyl, and linolenyl; $C_3$–$C_8$ cycloalkyl esters, including, but not limited to, cyclopropyl, cyclobutyl, cyclopentyl, cyclohexyl, cycloheptyl, and cyclooctyl; aryl ester, including, but not limited to phenyl, toluyl, xylyl, and naphthyl; alicyclic esters, including, but not limited to, menthyl; and aralkyl esters, including, but not limited to benzyl, and phenethyl.

The term "alendronate" as used herein, denotes the disphosphate compound 4-amino-1-hydroxybutylidene-1,1-bisphosphonic acid and its pharmaceutically-acceptable salts, i.e. monosodium trihydrate. The compound alendronate is further described in U.S. Pat. Nos. 4,922,007 and 5,019,651 both issued to Merck and both hereby incorporated by reference.

Generally speaking, the proper selection of the active ingredient depends on the selected type of formulation, the disease pattern, especially the site and type of the disease, and the desired release of the active ingredient. In addition, the physical and chemical characteristics of the active ingredient must be taken into account when selecting suitable pharmaceutically-acceptable excipients for use in the novel dosage forms containing the active ingredient.

The effective oral dose of the active ingredient depends on the extent of the disease. For examples, for adults the amount of risedronate usually amounts to from about 1 mg to about 40 mg daily, preferably from about 1 mg to about 30 mg daily. When the dose is to be administered continuously, the preferred dose is from 1–15 mg/day, preferably from 1–10 mg/day. When the dose is to be administered cyclically, the dose is preferably from 5–40 mg/day, preferably from 10–30 mg/day.

B. Site of Delivery of the Active Ingredient

A human or other mammal suffering from various diseases or disorders can be successfully treated by the delivery of the novel dosage form containing the active ingredient to the stomach of said human or other mammal. The novel oral generally oval shaped, film coated dosage forms described herein facilitate rapid transit through the esophagus thus effectively delivering the dosage form to the stomach and avoiding or minimizing the undesired release of risedronate in the mouth, pharynx and/or the esophagus thereby prohibiting the erosion, ulceration or other like irritation of the epithelial or mucosal layers of these tissues. The term "gastrointestinal tract" as used herein relates to the alimentary canal, i.e., that musculo-membranous tube about thirty feet in length, extending from the mouth to the anus. The term "upper gastrointestinal tract" as used herein means the buccal cavity, the pharynx, the esophagus, and the stomach. The term "lower gastrointestinal tract" as used herein means the small intestine, and the large intestine.

The term "buccal cavity" means the mouth or oral cavity and is lined with a mucous membrane which is continuous with the integument of the lips and with the mucous lining of the pharynx.

The term "pharynx" relates to the part of the upper gastrointestinal tract which is placed behind the nose, mouth and larynx. It is a mucomembraneous tube about 4 inches in length and posteriority with the esophagus and is composed of a mucous coat, a fibrous coat, and a muscular coat.

The term "esophagus" as used herein is a muscular canal about nine inches long extending from the pharynx to the stomach. The esophagus has three coats; and internal mucous coat surrounding the lumen, a middle aveolar coat and an external muscular coat.

The term "stomach" as used herein means that part of the gastrointestinal tract between the esophagus and the small intestine.

C. The Film Coating

The term "film-coated" as used herein relates to a mixture of pharmaceutically-acceptable excipients which is applied to, combined with, mixed with or otherwise added to the active ingredients. The said coating may be applied to a compressed tablet, beads, granules, or particles of active ingredient that are compressed into tablets. The coating chosen must be compatible with the particular active ingredient selected.

Accordingly, the said film coating is preferably applied to a compressed tablet which contains particles or granules of active ingredient; however, in the event the particles or granules are themselves film-coated before being compressed into a tablet, then the film coating of the compressed tablet itself is optional. Because of their film coating, these novel dosage forms will avoid the undesirable delivery of the active ingredient to the mucosal and epithelial tissues of the upper gastrointestinal tract, especially the mouth, pharynx and esophagus. Said coating also achieves the delivery of the active to the stomach which can be manipulated by one skilled in the art by choosing the excipients which make up the coating, its type, and/or its thickness.

Preferred polymers for film-coating are soluble at pH of from about 1.2 to about 5. Particularly preferred polymers are selected from the group consisting of hydroxypropylmethylcellulose (HPMC) alone and/or in combination with hydroxypropylcellulose (HPC), carboxymethylcellulose, methylcellulose, ethylcellulose, acrylic resins, and polyvinylpyrrolidone and gelatin or other commercially available film-coating preparations such as Dri-Klear, manufactured by Crompton & Knowles Corp., Mahwah, N.J. or Opadry manufactured by Colorcon, West Point Pa. Particularly preferred are HPMC, HPC, Dri-Klear and 30 Opadry. The lower viscosity HPMC's grades, E-5 and the E-15 are the preferred grades and the most preferred is the E-5 grade. The preferred concentration of the polymer in the coating suspension is controlled to yield a viscosity of between 50–250 cps.

The amount of coating deposited on the tablet is usually in the range of from about 2% to about 5% weight gain with a preferred weight gain of about 3%. The coating can, and usually will, contain a plasticizer. The preferred plasticizers are polyethylene glycol and polypropylene glycol and the most preferred plasticizer is polyethylene glycol. The preferred amount of plasticizer is from about 15% to about 40% with respect to the film-forming polymer, with the most preferred level of about 20%. Dyes or pigments may also be added to provide the required opacity and color to the film-coating. The preferred level of the pigment is from about 10% to about 40% with respect to the film-forming polymer, with the most preferred level of from about 20% to about 30%. Other additives may be added to minimize foam or to facilitate spraying of the solution on the tablets.

D. Novel Generally Oval Shaped, Film Coated Oral Dosage Forms for Delivery of the Active Ingredient Containing Dosage Form to the Stomach As stated hereinabove, the present invention is directed to novel generally oval shaped, film-coated oral dosage forms of an active ingredient to effect delivery to the stomach of a human or other mammal. The novel generally oval shaped, film-coated dosage form facilitates rapid transit through the upper gastrointestinal tract and avoids the delivery of the active ingredient until it reaches the stomach of the individual. Upon reaching the stomach the dosage form dissolves and absorbtion of the active ingredient through the small and/or large intestine can be achieved. Thus, tissues of the upper gastrointestinal tract, especially the epithelial and mucosal layers of the buccal cavity, the pharynx and esophagus are spared direct contact with the active ingredient and the active ingredient is absorbed at the appropriate site. Said oral dosage form, therefore, substantially alleviates the esophagitis or esophageal irritation which occasionally occurs upon oral administration of pharmaceutical compositions containing certain active ingredients.

Figure 2:
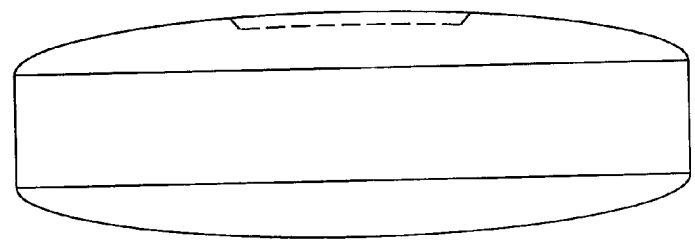
FIG. 2 is a side elevation view thereof.
Figure 3:
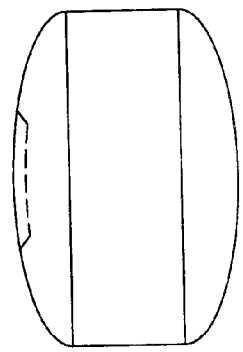
FIG. 3 is an end view of said modified oval tablet.

Accordingly, oral dosage forms suitable for use herein are generally oval shaped, preferably modified oval shape and are film coated. A modified oval dosage form is demonstrated in FIGS. 1–3. The dosage forms are formulated with active ingredients along with suitable pharmaceutical excipients which are well-known to those skilled in the art as described hereinbelow and are formed into the appropriate shape using apparatuses and/or methods which are well-known to those skilled in the art. The generally oval tablets have the following preferred dimensions: length from about 0.23 to about 0.85 inches preferably from about 0.25 to about 0.75 inches, width from about 0.11 to about 0.4 inches preferably from about 0.15 to about 0.35 inches, and a thickness of from about 0.075 to about 0.3 inches, preferably from about 0.10 to about 0.25 inches. The modified oval tablet as shown in FIGS. 1–3 may have the following dimensions: a length of about 0.455 inches, width of about 0.225 and a thickness of approximately 0.157 inches.

The term "pharmaceutical composition" means an oral dosage form comprised of a safe and effective amount of an active ingredient and pharmaceutically-acceptable excipients. The pharmaceutical compositions described herein are comprised of from about, 0.1% to about 99%, preferably from about 0.5% to about 95% of an active ingredient, and from about 1% to about 99.9%, preferably from 5.00% to about 99.90% of pharmaceutically-acceptable excipients. For risedronate the composition comprises, preferably 0.25% to 40%, preferably from about 0.5% to about 30% of a risedronate active ingredient and from about 60% to about 97%, preferably from about 70% to about 99.5% of pharmaceutically-acceptable excipients.

The phrase "safe and effective amount", as used herein means an amount of a compound or composition high enough to significantly positively modify the symptoms and/or condition to be treated, but low enough to avoid serious side effects (at a reasonable benefit/risk ratio), within the scope of sound medical judgment. The safe and effective amount of active ingredient for use in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular active ingredient selected for use. Pharmaceutically-acceptable excipients include, but are not limited to, polymers, resins, plasticizers, fillers, lubricants, binders, disintegrants, solvents, co-solvents, buffer systems, surfactants, preservatives, sweetening agents, flavoring agents, pharmaceutical grade dyes and pigments. All or part of the pharmaceutically-acceptable excipients contained in the pharmaceutical compositions described herein is used to make the film coating which is to be utilized in the novel oral dosage forms described herein.

The term "oral dosage form" as used herein means any pharmaceutical composition intended to be administer to the stomach of an individual via the mouth of said individual, and for purposes of the present invention, the delivered form is in the form of a modified oval tablet (preferably film coated) containing granules or particles of active ingredient.

"Film-coated oral dosage form" as used herein relates to an oral dosage form containing a pharmaceutical composition as described herein which utilizes a film coating to effect the release of the active ingredient in the stomach. The film-coated oral dosage from is a compressed tablet containing granules or particles of the active ingredient, which may be coated or uncoated.

The term "rapid esophageal transit" as used herein means the time it takes for a tablet to pass from the oropharynx to the stomach. Rapid esophageal transit would comprise of transit less than about 90 seconds, preferably from about 1 to about 60 seconds. Most preferred is less than 20 seconds when taken with 50 ml of water.

As stated hereinabove, the ultimate site of topical delivery in the stomach can be satisfactorily controlled by one skilled in the art, by manipulating any one or more of the following:

(a) The active ingredient proper;

(b) the type of the coating, and the concomitant desirable thickness and permeability (swelling properties) of said coating;

(c) the time-dependent conditions of the coating itself and/or within the coated tablet, particle, bead, or granule; and (d) the particle size of the granulated active ingredient.

As stated hereinabove, pharmaceutically-acceptable excipients include, but are not limited to polymers, resins, plasticizers, fillers, lubricants, binders, disintegrants, solvents, cosolvents, surfactants, preservatives, sweetener agents, flavoring agents, buffer systems, pharmaceutical-grade dyes and pigments.

The preferred solvent is water.

Flavoring agents among those useful herein include those described in *Remington's Pharmaceutical Sciences,* 18th Edition, Mack Publishing Company, 1990, pp. 1288–1300, incorporated by reference herein. Dyes, or pigments among those useful herein include those described in *Handbook of Pharmaceutical Excipients,* Second Edition pp. 126–134, 1994 by the American Pharmaceutical Association & the Pharmaceutical Press, incorporated by reference herein.

Preferred co-solvents include, but are not limited to, ethanol, glycerin, propylene glycol, polyethylene glycol.

Preferred buffer systems include, but are not limited to potassium acetate, boric carbonic, phosphoric, succinic, malic, tartaric, citric, acetic, benzoic, lactic, glyceric, gluconic, glutaric and glutamic. Particularly preferred are phosphoric, tartaric, citric, and potassium acetate.

Preferred surfactants include, but are not limited to, polyoxyethylene sorbitan fatty acid esters, polyoxyethylene monoalkyl ethers, sucrose monoesters and lanolin esters and ethers.

Preferred preservatives include, but are not limited to, phenol, alkyl esters of parahydroxybenzoic acid, benzoic acid and the salts thereof, boric acid and the thereof, sorbic acid and the salts thereof, chorbutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben.

Preferred sweeteners include, but are not limited to, sucrose, glucose, saccharin, and aspartame. Particularly preferred are sucrose and saccharin.

Preferred binders include, but are not limited to methycellulose, sodium carboxymethycellulose, hydroxypropylmethylcellulose, carbomer, providone, acacia, guar gum, xanthan gum and tragacanth. Particularly preferred are methycellulose, carbomer, xanthan gum, guar gum, povidone and sodium carboxymethycellulose.

Preferred fillers include, but are not limited to lactose, sucrose, maltodextrin, mannitol, starch, and microcrystalline cellulose.

Preferred plasticizers include, but are not limited to polyethylene glycol, propylene glycol, dibutyl phthalate, and castor oil, acetylated monoglycerides, and triacetin.

Preferred lubricants include, but are not limited to, magnesium stearate, stearic acid, and talc.

Preferred disintegrants include, but are not limited to, crospovidone, sodium carboxymethyl starch, sodium starch glycolate, sodium carboxymethyl cellulose, alginic acid, clays, and ion exchange resins.

Preferred polymers, include but are not limited to hydroxypropylmethylcellulose (HPMC) alone and/or in combination with hydroxypropylcellulose (HPC), carboxymethylcellulose, acrylic resins such as Eudragit® RL30D, manufactured by Rohm Pharma GmbH Weiderstadt, West Germany, methylcellulose, ethylcellulose, and polyvinylpyrrolidone or other commercially available film-coating preparations such as Dri-Klear, manufactured by Crompton & Knowles Corp., Mahwah, N.J. or Opadry manufactured by Colorcon, West Point, Pa.

Utilizing the novel oral dosage forms of the present invention, the active ingredient can be reliably delivered to the stomach thereby avoiding the undesirable exposure of the active in the mucosal and epithelial tissues of the mouth, pharynx, and/or esophagus. Said dosage forms render the active ingredient readily available for absorption from the stomach and, there is substantially no contact of the active ingredient upon the epithelial and mucosal tissues of the mouth, pharynx, or esophagus. Accordingly, the novel modified oval, film-coated oral dosage form of the present invention substantially alleviates the condition of esophagitis or esophageal irritation which occasionally results from the oral administration of a pharmaceutical composition comprising certain active ingredients.

Any film-coating which is soluble in the gastric contents pH 1.2–5 can be used in the practice of the present invention. The preferred polymer to be used as the film coating must be applied to the compressed tablet, the gelatin capsule and/or beads, particles or granules of active ingredient in a sufficient thickness so that the entire coating dissolves in the stomach. The dissolution or disintegration of the excipient coating generally does not occur until the entry of the coated dosage form into the stomach.

The following non-limiting examples serve to further illustrate the novel oral dosage forms of the present invention.

EXAMPLE I

Modified Oval, Film-Coated Risedronate Tablet

The film-coating is applied to 110 kg of risedronate core tablets each weighing 240 mg.

| Component | kg/batch | mg/tablet |
| --- | --- | --- |
| Risedronate sodium tablets 30 mg | 110 | 240 |
| Dri-Klear | 2.598 | 5.67 |
| Chroma-Tone White | 0.701 | 1.53 |
| Purified Water | 30.2 kg | 65.9 |

Dri-Klear is a mixture of HPMC, RPC, polyethylene glycol, and silicon dioxide manufactured by Crompton and Knowles, Marwah, N.J., Chroma-Tone White is a mixture of HPC and titanium dioxide manufactured by Crompton and Knowles, Marwah, N.J.

The coating suspension is prepared as follows:

1. Add the Dri-Klear to hot purified water, 60–80° C., with agitation.
2. Cool the Dri-Klear solution to 40° C. or below, with continual mixing until all the Dri-Klear is dissolved.

3. Add the Chroma-Tone White to purified water with mixing. Disperse with the use of a high shear mixer for 10–25 minutes.
4. Add the pigment suspension (step 3) to the polymer solution (step 2) and mix. Continue mixing until ready for use.
5. Load the core tablets into a 48 inch side vented coating pan.
6. Preheat the tablets until the exhaust temperature reaches approximately 35° C. and begin spraying. Apply the coating suspension using an inlet air temperature of 40–60° C. at a rate of 300–400 g/minute.
7. Cool the tablets and discharge.

EXAMPLE II

Caplet Shaped, Film-Coated Alendronate Tablet

The film-coating is applied to 100 kg of alendronate core tablets each weighing 200 mg.

| Component | kg/batch | mg/tablet |
| --- | --- | --- |
| Alendronate sodium tablets 10 mg | 100 | 200.0 |
| Opadry | 5.0 | 10.0 |
| Red iron oxide | 0.1 | 0.2 |
| Purified Water | 50 kg | 100 |

Opadry is a commercial film-coating mixture manufactured by Colorcon, West Point, Pa. The coating suspension is prepared as follows:
1. Add the Opadry to room temperature purified water with agitation.
2. Mix until all the Opadry is dissolved.
3. Add the red iron oxide to purified water with mixing. Disperse with the use of a high shear mixer for 5 minutes.
4. Add the red iron oxide suspension (step 3) to the polymer solution (step 2) and mix. Continue mixing until ready for use.
5. Load the core tablets into a 48 inch side vented coating pan.
6. Preheat the tablets until the exhaust temperature reaches approximately 40° C. and begin spraying. Apply the coating suspension using an inlet air temperature of 40–60° C. at a rate of 250–350 g/minute.
7. Cool the tablets and discharge.

EXAMPLE III

Oval Risedronate Tablets

The film-coated risedronate tablets are made by preparing granules containing the active. coating the granules, compressing into a tablet and then film-coating the tablets.
A. Preparation of the Risedronate Sodium Granules, 212.5 kg

| Component | kg/batch | mg/g (Dry basis) |
| --- | --- | --- |
| Risedronate sodium | 2.5 | 11.7 |
| Lactose, anhydrous | 100 | 471 |
| Microcrystalline cellulose | 100 | 471 |
| Polyvinylpyrrolidone | 10 | 47.1 |
| Purified Water | 75 kg | — |

The granulation is prepared as follows:
1. Dissolve the polyvinylpyrrolidone in the purified water.
2. Mix the risedronate sodium, lactose and microcrystalline cellulose in a high shear mixer for 3 minutes.
3. Granulate the mixture with the polyvinylpyrrolidone solution with mixing over a 5 minute interval.
4. Dry the wetted mass in a fluid bed dryer at an inlet temperature of 60° C.
5. Mill the dried material using a hammer mill to achieve the desired granule size.
B. Coating of the Granules and Preparation of Risedronate Sodium Tablets, 130.3 kg

| Component | kg/batch | mg/tablet |
| --- | --- | --- |
| Risedronate sodium granules | 106.8 | 213.6 |
| Hydroxypropylmethylcellulose E-15 | 5 | 10.0 |
| Purified Water | 50 | 100. |
| Crospovidone | 3 | 6.0 |
| Microcrystalline cellulose | 15 | 30.0 |
| Magnesium Stearate | 0.5 | 1.0 |

The granulation is coated and compressed into tablets as follows:
1. Dissolve the hydroxypropylmethylcellulose E-15 in purified water at 60° C. with continued mixing. Cool to 30° C. and mix until dissolved.
2. Add the risedronate sodium granules to a suitable coating column.
3. Spray on the hydroxypropylmethylcellulose E-15 solution at an inlet temperature of 50° C. After coating, dry the coated granules at an inlet temperature of 60° C.
4. Transfer the coated granules to a twin shell blender and add the crospovidone and microcrystalline cellulose and mix for 5 minutes.
5. Add the magnesium stearate and mix for 3 minutes and compress into tablets on a rotary press.
C. Film-coating
Film-coating is applied to 120 kg of risedronate core tablets each weighing 260.6 mg.

| Component | kg/batch | mg/tablet |
| --- | --- | --- |
| Risedronate sodium tablets 2.5 mg | 120 | 260.6 |
| Hydroxypropylmethylcellulose E-5 | 2.3 | 5.0 |
| Polyethylene glycol 6000 | 0.92 | 2.0 |
| FD&C Blue # 1 Lake | 0.05 | 0.1 |
| Silicon dioxide | 0.05 | 0.1 |
| Purified Water | 50 kg | 109 |

The coating suspension is prepared as follows:
1. Add the hydroxypropylmethylcellulose E-5 to a portion of the purified water at 80° C., with agitation. Add the remaining purified water at 10° C. and mix until dissolved.
2. Add the polyethylene glycol 6000 to purified water with mixing.
3. Add the FD&C Blue #1 lake and the silicon dioxide to the polyethylene glycol solution. Disperse with the use of a high shear mixer for 10–25 minutes.
4. Add the pigment suspension (step 3) to the polymer solution (step 1) and mix.
5 Load the core tablets into a 48 inch side vented coating pan.
6. Preheat the tablets until the exhaust temperature reaches approximately 40° C. and begin spraying.

Apply the coating suspension using an inlet air temperature of 40° C. at a rate of 250 g/minute.

7. Cool the tablets and discharge.

What is claimed is:

1. An oral dosage form to be delivered to the stomach said dosage form comprising a safe and effective amount of alprenolol and pharmaceutically-acceptable excipients, wherein said oral dosage form is oval shaped, about 0.23 to about 0.85 inches in length, about 0.11 to about 0.4 inches in width, and about 0.075 to about 0.3 inches in thickness and said oral dosage form is film coated to facilitate rapid esophageal transit and avoid irritation in the mouth, buccal cavity, pharynx, and esophagus wherein said film coating allows for delivery of said alprenolol to the stomach.

2. A dosage form according to claim 1 wherein the film coating is soluble at pH from about 1.2 to about 5.

3. A dosage form according to claim 2 wherein said film coating is selected from the group consisting of hydroxypropylmethylcellulose, hydroxypropylcellulose, carboxymethylcellulose, methylcellulose, ethylcellulose, acrylic resins, polyvinylpyrrolidone or gelatin or mixtures thereof.

4. A dosage form according to claim 1 wherein said film coating is selected from the group consisting of hydroxypropylmethylcellulose and hydroxypropylcellulose.

5. An oral dosage form according to claim 1 wherein said dosage form is a compressed tablet comprising particles of alprenolol and pharmaceutically-acceptable excipients.

6. An oral dosage form according to claim 5 wherein said particles of alprenolol are themselves film coated.

7. An oral dosage form according to claim 4 wherein the length is about 0.455 inches, the width of about 0.255 inches and the thickness about 0.157 inches.

* * * * *

UNITED STATES PATENT AND TRADEMARK OFFICE
CERTIFICATE OF CORRECTION

PATENT NO. : 6,569,460 B1
DATED : May 27, 2003
INVENTOR(S) : Richard John Dansereau et al.

It is certified that error appears in the above-identified patent and that said Letters Patent is hereby corrected as shown below:

Column 8,
Line 58, "RPC" should read -- HPC --

Signed and Sealed this

Twelfth Day of August, 2003

JAMES E. ROGAN
*Director of the United States Patent and Trademark Office*